United States Patent [19]

Kawase et al.

[11] 4,235,529
[45] Nov. 25, 1980

[54] APPARATUS FOR RECORDING IMAGES OF CRYSTALLINE LENS SECTIONS

[75] Inventors: Suminosuke Kawase, Ohmiya; Yukinori Karasawa, Yokohama, both of Japan

[73] Assignee: Tokyo Kogaku Kikai Kabushiki Kaisha, Tokyo, Japan

[21] Appl. No.: 879,952

[22] Filed: Feb. 21, 1978

[30] Foreign Application Priority Data

Feb. 21, 1977 [JP] Japan .................................. 52-18511

[51] Int. Cl.³ .......................... A61B 3/10; A61B 3/14; G03B 29/00
[52] U.S. Cl. .......................................... 351/14; 351/7; 351/16; 354/62
[58] Field of Search .................. 351/14, 7, 16; 354/62

[56] References Cited

U.S. PATENT DOCUMENTS

| 3,536,383 | 10/1970 | Cornsweet et al. | 351/16 X |
| 3,586,424 | 6/1971 | Schenk et al. | 351/9 |
| 3,762,803 | 10/1973 | Papritz | 351/14 X |
| 3,925,793 | 12/1975 | Matsumura et al. | 351/7 X |

Primary Examiner—John K. Corbin
Assistant Examiner—Rodney Bovernick
Attorney, Agent, or Firm—Stevens, Davis, Miller & Mosher

[57] ABSTRACT

Apparatus for taking photographs of crystalline lens sections including a slit illumination system and a photographing optical system which includes an optical axis inclined with respect to the slit illumination plane. In order to eliminate an image of illumination light source which may be produced by a light reflected at the patient's cornea, a light interrupting blade member is provided in the illumination optical path at a side of the slit axis adjacent to the photographing optical system.

7 Claims, 3 Drawing Figures

APPARATUS FOR RECORDING IMAGES OF CRYSTALLINE LENS SECTIONS

The present invention relates to an apparatus for recording images of sections of crystalline lenses.

Hithertofore, in order to record images of sections of crystalline lenses, an apparatus has been proposed for taking photographs of such crystalline lens sections. Such apparatus for taking photographs of crystalline lens sections comprises a slit illumination system for illuminating a crystalline lens along a slit plane and a photographing system having an optical axis inclined with respect to the slit plane. In this type of apparatus, the slit illumination system includes a slit mask through which illumination light is projected. Further, in addition to the slit mask, a second slit mask is provided in or adjacent to the projecting lens so that the projecting depth of the illumination slit can be increased. This arrangement is effective to limit transverse spreading of the projected light, however, it is still possible that a portion of light which has been deviated from the slit plane is reflected at the corneal surface toward the photographing lens to produce an image of the light source on the image plane.

The present invention has therefore an object, to provide an apparatus for recording images of sections of crystalline lenses, in which the images of the light source are eliminated from the image plane in recording and utilized for accomplishing an exact alignment between the axis of the patient's eye and the optical axis of the slit projecting lens.

According to the present invention, the above and other objects can be accomplished by an apparatus for recording images of sections of crystalline lenses which comprises a slit illumination system for illuminating a crystalline lens along a slit illumination path including a slit plane having a slit axis, a recording optical system having an optical axis inclined with respect to the slit plane, light interrupting means provided in the illumination path at a side of the slit axis adjacent to the recording optical system so as to block a portion of light projected by the slit illumination system. According to a preferable feature of the present invention, the light interrupting means is movable between an operative position in which it is projected into the illumination path and an inoperative position in which it is retracted from the illumination path, and means is provided for actuating the interrupting means into the operative position when a record is being taken, for example, by photographing. The interrupting means may be comprised of a blade member and means may be provided for adjusting the projected operative position of the interrupting blade member.

The present invention is well applicable to an apparatus for taking photographs of sections of crystalline lenses, however, the utility of the present invention is not limited to such an application but the invention can also be applied to other types of apparatus wherein the images are magnetically recorded or maintained on an imaging tube for a certain period.

The above and other objects and features of the present invention will become apparent from the following descriptions of a preferred embodiment taking reference to the accompanying drawings, in which.

Figure 1:
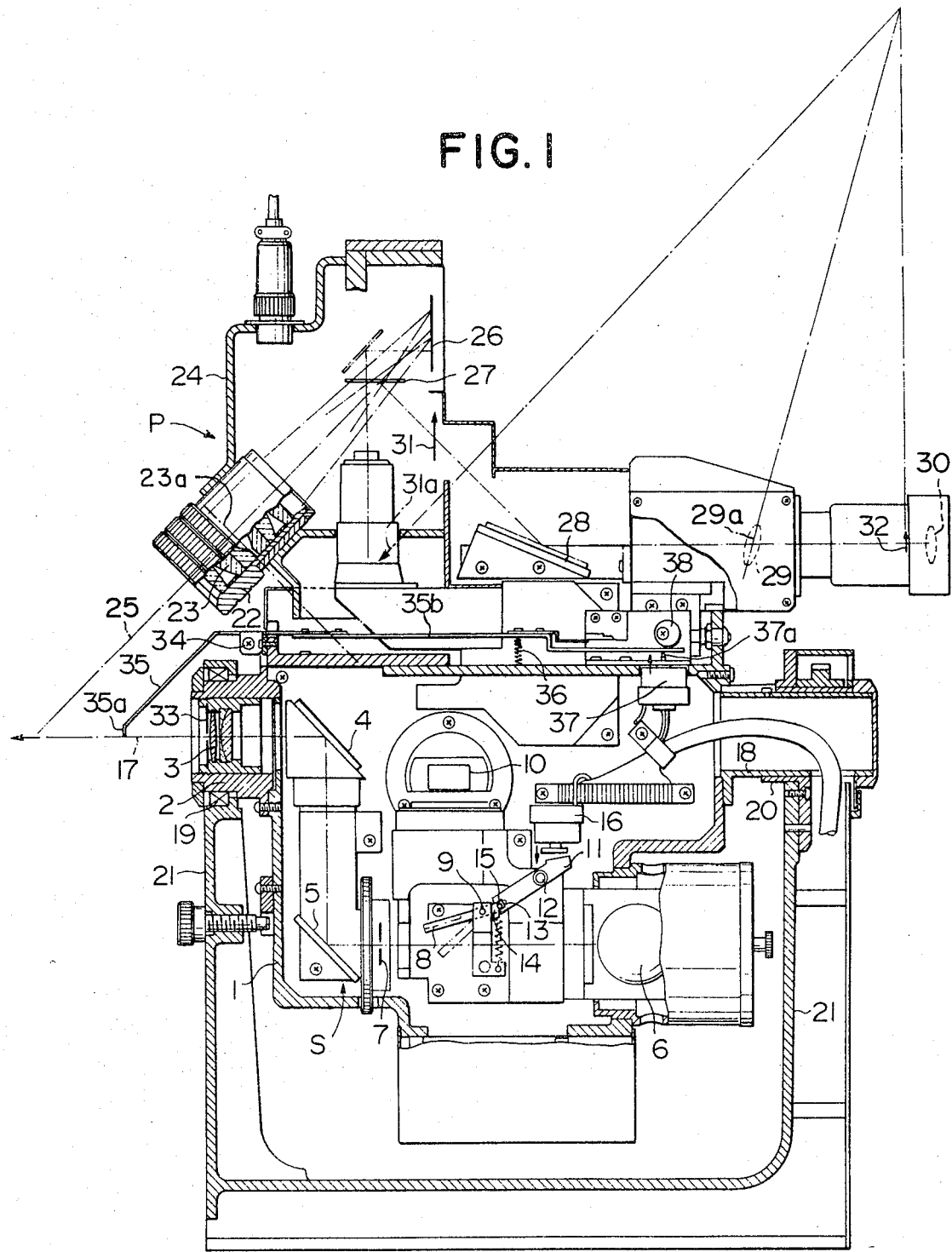
FIG. 1 is a sectional view of an apparatus for taking photographs of sections of crystalline lenses in accordance with one embodiment of the present invention.

Referring now to the drawings, particularly to FIG. 1, the apparatus in accordance with one embodiment of the present invention includes a slit illumination system S and a photographing optical system P which are disposed in a housing 1.

The slit illumination system S comprises a projecting lens 3 mounted in a lens tube 2 which is in turn fixed to the housing 1. Further, the system S includes reflecting mirrors 4 and 5 and an observation light source 6. A slit mask 7 is disposed between the mirror 5 and the light source 6. Between the slit mask 7 and the light source 6, there is disposed a reflecting mirror 8 which is movable about a pin 9 between a retracted position as shown by solid lines and an extended position as shown by dotted lines.

A photographing light source 10 is provided along the reflecting optical axis of the mirror 8 in the extended position. In order to move the mirror between the extended and retracted positions, an actuating lever 11 is provided. A second slit aperture plate 33 is disposed in the tube 2 of the projecting lens 3.

The actuating lever 11 is pivotably mounted by means of a shaft 12 and provided at one end with a groove 13 which engages a pin 15 on an extension of a frame 14 for the mirror 8. The other end of the actuating lever 11 is arranged so as to co-operate with a solenoid device 16 which serves when energized to force the corresponding end of the actuating lever 11 in the direction shown by an arrow so that the mirror 8 is moved to the extended or operative position shown by the dotted lines in FIG. 1.

The projecting lens 3 has an optical axis 17 which defines a slit axis and the housing 1 is provided at the rear portion with a shaft 18 of hollow cylindrical configuration. The shaft 18 is coaxial with the slit axis as well as with the lens tube 2 and the housing 1 is mounted at the lens tube 2 and the shaft 18 on a frame 21 by means of bearings 19 and 20. The housing 1 is therefore rotatable about the optical axis of the projecting lens 3 or the slit axis and the plane of the projected slit is also rotatable about the axis. The frame 21 is in turn mounted on a base structure for fore and aft, left and right and up and down movements in order to facilitate adjustment of the apparatus in aligning the visual axis of the patient's eye with the slit axis.

The photographing optical system P includes a photographing lens 23 mounted in a lens tube 22 which is rotatably supported in a camera housing 24 secured to the housing 1. In the illustrated embodiment, the lens 23 has an optical axis 25 which intersects the slit axis 17 at an angle of 45° and a film 26 is located on the photographing optical axis 25 within the camera housing 24. The film 26 is positioned in a plane which intersects the slit plane at a right angle and the photographing lens 23 is arranged in such a manner that the major plane 23a thereof intersects the plane of the film 26 at the intersection between the film plane and the slit plane.

The apparatus further includes a finder system which comprises a reflecting mirror 27 disposed between the photographing lens 23 and the film 26. The mirror 27 is movable between an operative or extended position as shown by solid lines and an inoperative or retracted position shown by dotted lines, and such movement of the mirror is effected in response to an actuation of the shutter mechanism in the photographing system.

In the operative position, the mirror 27 functions to reflect the light through the photographing lens 23. On the reflecting axis of the mirror 27, there is provided a second mirror 28 which reflects the light from the mirror 27 rearwardly in the direction parallel with the slit axis 17. Along the reflecting axis of the mirror 28, there are arranged a relay lens 29 and an eye lens 30.

The light which has passed through the photographing lens 23 produces, as shown by 31 in FIG. 1, an image of the crystalline lens of the patient's eye, said image corresponding to a section where the slit illumination is effected. The light from the image is reflected by the mirror 28 and passes through the relay lens 29 to produce a second image 32 which is observed through the eye lens 30. For the explanation of the finder system, consideration may be made of an apparent image 31a which is symmetrical with the image 31 with respect to the reflecting plane of the mirror 28. In the illustrated finder system, the relay lens 29 has a major plane 29a which passes through the intersection between the plane of the apparent image 31a and the plane of the second image 32. With this arrangement of the finder system, it is possible to focus the image throughout the image plane although the apparent image 31a is slanted with respect to the optical axis and the second image 32 is perpendicular thereto. The finder system is advantageous in that the first image 31 can be observed in the form of a space image and that a brighter image can be produced as compared with an arrangement wherein the first image is produced on an imaging plate.

According to the feature of the present invention, the illustrated apparatus includes means for preventing the light reflected at the cornea of the patient's eye from entering the photographing optical system P. This means comprises a reflection screening blade member 35 pivotably mounted on the housing 1 by means of a pin 34. The blade member 35 includes a screening blade edge 35a and a rearward extension 35b which is downwardly biased by means of a spring 36. The member 35 is therefore biased in clockwise direction about the axis of the pin 34 so that the blade edge 35a is normally maintained in the retracted position wherein it does not block the projected light through the lens 3.

A solenoid 37 is provided for co-operation with the rear end of the extension 35b on the blade member 35. The solenoid 37 has an actuating element 37a which serves to force the member 35 counterclockwise so as to move the blade edge 35a into the optical path of the slit projecting light when the solenoid is energized during photographing operation. An adjusting cam 38 is provided at a side of the extension 35b of the blade member 35 opposite to the side where the solenoid 37 is positioned. The cam 38 serves to limit the counterclockwise movement of the blade member 35 and consequently determine the position of the blade edge 35a in the projecting optical path.

Figure 2:
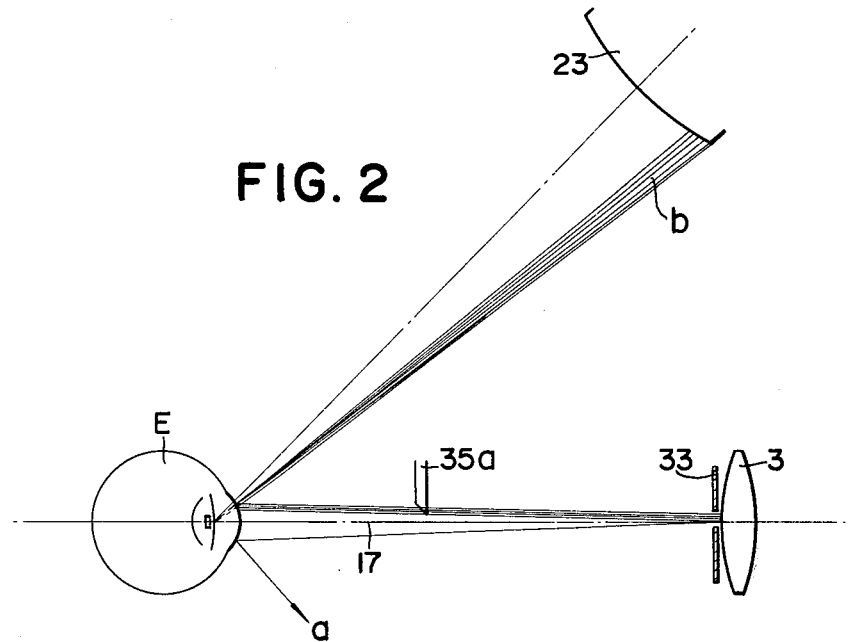
FIG. 2 is a diagrammatical view showing the effect of a reflection screening blade adopted in the apparatus shown in FIG. 1; and, FIG. 3 is a view specifically showing the positions of light source images which may be produced in the patient's eye.

Referring specifically to FIG. 2, it will be noted that, of the light which has passed through the second slit aperture plate 33 in front of the projecting lens 3, the portion which is at a side of the optical axis 17 opposite to the photographing lens 23 will be reflected at the cornea of the patient's eye E in the direction away from the photographing lens 23 as shown by an arrow a. Therefore, this particular light portion does not enter the photographing optical path after being reflected at the eye cornea. The light portion at the side of the slit axis 17 adjacent to the photographing lens 23 may be reflected toward the lens 23 so that this light portion is blocked by the blade edge 35a of the member 35. Thus, the arrangement is effective to prevent any corneal reflection from entering the photographing optical path.

Figure 3:
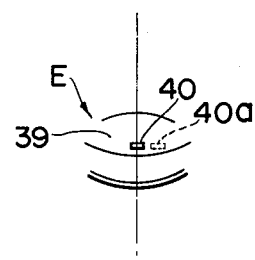

According to a further feature of the present invention, the blade edge 35a of the member 35 is moved to the operative position only during the photographing operation for the purpose described below. Referring to FIG. 3, an image of the projecting light source is produced in the crystalline lens 39 of the patient's eye E as shown by the numeral 40. When the slit axis 17 is not aligned with the visual axis of the patient's eye, the image of the light source will be offset from the axis of the eye as shown by 40a. Thus, the image 40 of the light source can be utilized for establishing an exact alignment between the slit axis 17 and the visual axis of the patient's eye E. In photographing, the blade edge 35a is moved into the slit projecting optical path so that the image 40 of the light source can be eliminated.

The invention has thus been shown and described with reference to specific embodiments, however, it should be noted that the invention is in no way limited to the details of the illustrated structures but changes and modifications may be made without departing from the scope of the appended claims. Thus, it should be construed that the invention broadly covers an apparatus comprising a slit projecting system and a recording optical system, said recording optical system including an optical axis inclined with respect to the slit illumination plane, and light interrupting means being provided at a side of the illuminating slit axis adjacent to the recording optical system so as to project into the illuminating optical path for preventing the light reflected at the cornea from entering the recording optical system.

We claim:

1. Apparatus for recording images of sections of crystalline lenses which comprises a slit illumination system for illuminating a crystalline lens along a slit illumination path including a slit plane having a slit axis, a recording optical system having an optical axis inclined with respect to the slit plane, light interrupting means in the illumination path between the objective lens means of the slit illumination system and the crystalline lens at a side of the slit axis adjacent to the recording optical system so as to selectively block a portion of light projected by the slit illumination system.

2. Apparatus in accordance with claim 1 in which said light interrupting means is movable between an operative position wherein it is projected into the illumination path and an inoperative position wherein it is retracted from the illumination path.

3. Apparatus in accordance with claim 2 in which means is provided for actuating the interrupting means into the operative position when a record is being taken.

4. Apparatus in accordance with claim 1 in which said recording optical system is a photographing system.

5. Apparatus in accordance with claim 1 in which said interrupting means comprises a blade member having an edge adapted to be positioned in the illumination path.

6. Apparatus in accordance with claim 1 in which means is provided for adjusting position of the light illuminating means.

7. Apparatus in accordance with claim 6 in which said adjusting means is cam means.

* * * * *